(12) United States Patent
Llop

(10) Patent No.: US 10,405,945 B2
(45) Date of Patent: Sep. 10, 2019

(54) BONE FOUNDATION GUIDE AND METHOD OF USE

(71) Applicant: NATIONAL DENTEX, LLC, Palm Beach Gardens, FL (US)

(72) Inventor: Daniel R. Llop, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 848 days.

(21) Appl. No.: 14/495,304

(22) Filed: Sep. 24, 2014

(65) Prior Publication Data

US 2015/0010881 A1    Jan. 8, 2015

Related U.S. Application Data

(63) Continuation-in-part of application No. 14/214,555, filed on Mar. 14, 2014.
(Continued)

(51) Int. Cl.
*A61C 8/00* (2006.01)
*A61C 1/08* (2006.01)

(52) U.S. Cl.
CPC ............ *A61C 1/084* (2013.01); *A61C 8/0089* (2013.01)

(58) Field of Classification Search
CPC ....... A61C 1/084; A61C 1/082; A61C 8/0048; A61C 8/0089; A61C 8/005; A61C 13/2656; A61C 13/225; A61C 13/10; A61C 13/26
(Continued)

(56) References Cited

U.S. PATENT DOCUMENTS 5,018,970 A * 5/1991 Stordahl .............. A61C 8/0089
433/116
5,725,376 A    3/1998 Poirier
(Continued)

FOREIGN PATENT DOCUMENTS

CA    2795668 A1    11/2011
CA    2934371 A1    6/2015
(Continued)

OTHER PUBLICATIONS

Online video of zygomatic dental implant surgery: http://www.youtube.com/watch?v=TGBxbP9aa2g&sns=em Title Zygomatic Implant Guided Surgery—Noris Medical, Published on Mar. 11, 2015, 1 pg.
(Continued)

*Primary Examiner* — Heidi M Eide
*Assistant Examiner* — Mirayda A Aponte
(74) *Attorney, Agent, or Firm* — Frost Brown Todd, LLC

(57) ABSTRACT

A bone foundation guide with a bone foundation guide body contoured to guide a cutting implement to alter an exposed bone of a dental surgical site. The bone foundation guide body may form an encircled open surgical space that continuously connects a top and a bottom of the bone foundation guide body. The bottom may be further contoured to affix to the exposed bone of the dental surgical site while the top is further adapted to support a dental implant surgical guide or in the alternative a cutting containment guard. The cutting containment guard may have a cutting channel for receiving the exposed bone when the cutting containment guard is combined with the bone foundation guide body. The combination forms a cutting slot for guiding a cutting edge of a cutting implement to alter the exposed bone from the dental implant surgical guide.

20 Claims, 11 Drawing Sheets

Related U.S. Application Data

(60) Provisional application No. 61/784,029, filed on Mar. 14, 2013.

(58) Field of Classification Search
USPC ......... 433/72, 167–176, 201.1, 199.1, 200.1, 433/181, 182; 264/16–20
See application file for complete search history.

(56) References Cited

U.S. PATENT DOCUMENTS

| | | | |
|---|---|---|---|
| 5,967,777 | A | 10/1999 | Klein et al. |
| 6,319,006 | B1 | 11/2001 | Scherer et al. |
| 6,382,975 | B1 | 5/2002 | Poirier |
| 6,491,696 | B1 | 12/2002 | Kunkel |
| 6,672,870 | B2 | 1/2004 | Knapp |
| 6,814,575 | B2 | 11/2004 | Poirier |
| 6,997,707 | B2 | 2/2006 | Germanier |
| 7,331,786 | B2 | 2/2008 | Poirier |
| 7,632,097 | B2 | 12/2009 | De Clerck |
| 7,774,084 | B2 | 8/2010 | Cinader, Jr. |
| 7,824,181 | B2 | 11/2010 | Sers |
| 7,866,980 | B2 | 1/2011 | Poirier |
| 7,887,327 | B2 | 2/2011 | Marotta |
| 7,905,726 | B2 | 3/2011 | Stumpel |
| 7,909,606 | B2 | 3/2011 | Marcello |
| 7,942,668 | B2 | 5/2011 | Brajnovic et al. |
| 8,011,927 | B2 | 9/2011 | Berckmans, III et al. |
| 8,021,153 | B2 | 9/2011 | Poirier |
| 8,038,440 | B2 | 10/2011 | Swaelens et al. |
| 8,135,492 | B2 | 3/2012 | Yau et al. |
| 8,142,189 | B2 | 3/2012 | Brajnovic |
| 8,352,060 | B2 | 1/2013 | Chun et al. |
| 8,364,301 | B2 | 1/2013 | Schmitt |
| 8,371,849 | B2 | 2/2013 | Gao |
| 8,529,255 | B2 | 9/2013 | Poirier et al. |
| 8,540,510 | B2 | 9/2013 | Brajnovic |
| 8,574,302 | B2 | 11/2013 | McKay |
| 8,585,402 | B2 | 11/2013 | Vogel et al. |
| 8,706,672 | B2 | 4/2014 | Malfliet et al. |
| 8,770,972 | B2 | 7/2014 | Swaelens et al. |
| 8,827,699 | B2 | 9/2014 | Bavar |
| 8,899,984 | B2 | 12/2014 | Llop et al. |
| 9,069,914 | B2 | 6/2015 | Kopelman et al. |
| 9,107,723 | B2 | 8/2015 | Hall et al. |
| 9,155,548 | B2 | 10/2015 | Lin |
| 9,155,599 | B2 | 10/2015 | Thompson et al. |
| 9,161,822 | B2 | 10/2015 | Stevens et al. |
| 9,168,112 | B2 | 10/2015 | Haber |
| 9,173,723 | B2 | 11/2015 | Harrison |
| 9,211,165 | B2 | 12/2015 | Jamison |
| 9,226,801 | B2 | 1/2016 | Groscurth et al. |
| 9,259,291 | B2 | 2/2016 | Gantes |
| 9,308,055 | B2 | 4/2016 | Fisker et al. |
| 9,336,336 | B2 | 5/2016 | Deichmann et al. |
| 9,358,082 | B2 | 6/2016 | Nilsson |
| 9,381,072 | B2 | 7/2016 | Furrer et al. |
| 9,402,698 | B2 | 8/2016 | Thompson et al. |
| 9,498,307 | B2 | 11/2016 | Harrison |
| 9,504,533 | B2 | 11/2016 | Groscurth et al. |
| 2006/0166169 | A1 | 7/2006 | Dawood |
| 2007/0162014 | A1* | 7/2007 | Campbell ............ A61B 17/663 606/285 |
| 2009/0092948 | A1 | 4/2009 | Gantes |
| 2009/0130630 | A1* | 5/2009 | Suttin .................... A61C 1/084 433/174 |
| 2009/0274990 | A1 | 11/2009 | Kim |
| 2009/0298008 | A1 | 12/2009 | Groscurth et al. |
| 2010/0035201 | A1 | 2/2010 | Beck et al. |
| 2010/0124731 | A1 | 5/2010 | Groscurth et al. |
| 2010/0316974 | A1 | 12/2010 | Yau et al. |
| 2011/0033819 | A1 | 2/2011 | Freyer et al. |
| 2011/0045431 | A1 | 2/2011 | Groscurth et al. |
| 2011/0045432 | A1 | 2/2011 | Groscurth et al. |
| 2011/0111371 | A1 | 5/2011 | Haber |
| 2011/0151399 | A1 | 6/2011 | De Clerck et al. |
| 2011/0256508 | A1 | 10/2011 | Gantes |
| 2012/0046914 | A1 | 2/2012 | Gao |
| 2012/0053593 | A1 | 3/2012 | Abboud |
| 2012/0156638 | A1 | 6/2012 | Gantes |
| 2012/0261848 | A1 | 10/2012 | Haraszati |
| 2012/0277899 | A1 | 11/2012 | Chun et al. |
| 2013/0011813 | A1 | 1/2013 | Garcia et al. |
| 2013/0023888 | A1 | 1/2013 | Choi et al. |
| 2013/0209956 | A1 | 8/2013 | Sanders |
| 2013/0252202 | A1 | 9/2013 | Pardeller et al. |
| 2014/0026419 | A1 | 1/2014 | Haber |
| 2014/0080086 | A1 | 3/2014 | Chen |
| 2014/0080092 | A1 | 3/2014 | Suttin et al. |
| 2014/0099599 | A1 | 4/2014 | Harrison et al. |
| 2014/0255873 | A1 | 9/2014 | Bullis et al. |
| 2014/0255876 | A1 | 9/2014 | Alpern et al. |
| 2014/0272778 | A1 | 9/2014 | Llop |
| 2014/0272779 | A1 | 9/2014 | Okay |
| 2014/0272780 | A1 | 9/2014 | Llop |
| 2015/0025855 | A1 | 1/2015 | Fisker et al. |
| 2015/0030995 | A1 | 1/2015 | Villa |
| 2015/0037756 | A1 | 2/2015 | Berckmans, III et al. |
| 2015/0093717 | A1 | 4/2015 | Ali |
| 2015/0111179 | A1 | 4/2015 | Suttin |
| 2015/0133956 | A1 | 5/2015 | Dayan et al. |
| 2015/0150684 | A1* | 6/2015 | De Clerck ............ A61F 2/2803 623/17.17 |
| 2015/0230894 | A1 | 8/2015 | Juzbasic et al. |
| 2015/0265372 | A1 | 9/2015 | Kim et al. |
| 2015/0272704 | A1 | 10/2015 | Watson et al. |
| 2015/0272705 | A1 | 10/2015 | Watson et al. |
| 2015/0302170 | A1 | 10/2015 | Berckmans, III et al. |
| 2015/0359614 | A1 | 12/2015 | Sachdeva et al. |
| 2015/0374460 | A1 | 12/2015 | Sachdeva et al. |
| 2016/0008110 | A1 | 1/2016 | Harrison |
| 2016/0038255 | A1 | 2/2016 | Llop |
| 2016/0106517 | A1 | 4/2016 | Groscurth et al. |
| 2016/0106518 | A1 | 4/2016 | Choi et al. |
| 2016/0128810 | A1 | 5/2016 | Fostick et al. |
| 2016/0157967 | A1 | 6/2016 | Kim et al. |
| 2016/0157970 | A1 | 6/2016 | Gantes |
| 2016/0278878 | A1 | 9/2016 | Watson et al. |
| 2016/0287336 | A1 | 10/2016 | Kim et al. |
| 2016/0324599 | A1 | 11/2016 | Harrison |
| 2016/0045280 | A1 | 12/2016 | Haber |
| 2017/0071697 | A1 | 3/2017 | Groscurth et al. |
| 2017/0112591 | A1 | 4/2017 | Llop |
| 2017/0112592 | A1 | 4/2017 | Groscurth et al. |
| 2017/0252126 | A1 | 9/2017 | Llop |

FOREIGN PATENT DOCUMENTS

| | | |
|---|---|---|
| EP | 2 425 797 A1 | 3/2012 |
| MX | 2014001163 A | 7/2015 |
| WO | WO 2010/061391 | 6/2010 |
| WO | WO 2012/007615 | 1/2012 |
| WO | WO 2014/130536 | 8/2014 |
| WO | WO 2015/148891 | 10/2015 |

OTHER PUBLICATIONS

Select pages showing a bone reduction guide from the publication Art of Computer Guided Implantology by Tradiev and Rosenfield, Copyright 2009, 3 pgs.

Website showing a bone reduction guide that was uploaded by www.dentalinformation.com on Aug. 4, 2011 located at https://www.youtube.com/watch?v=AZnReFZmLN8 the upload is entitled Bone Reduction and Bone Supported Guide for Guided Dental Implant Surgery, 1 pg.

International Search Report and Written Opinion dated Mar. 2, 2016 for Application No. PCT/US2015/061002, 14 pgs.

International Search Report and Written Opinion dated Jul. 26, 2016 for Application No. PCT/US2016/021097, 13 pgs.

International Search Report and Written Opinion dated Jun. 16, 2017 for Application No. PCT/US2017/020746, 13 pgs.

(56) References Cited

OTHER PUBLICATIONS

International Search Report and Written Opinion dated Dec. 28, 2017 for Application No. PCT/US2017/054804, 10 pgs.

* cited by examiner

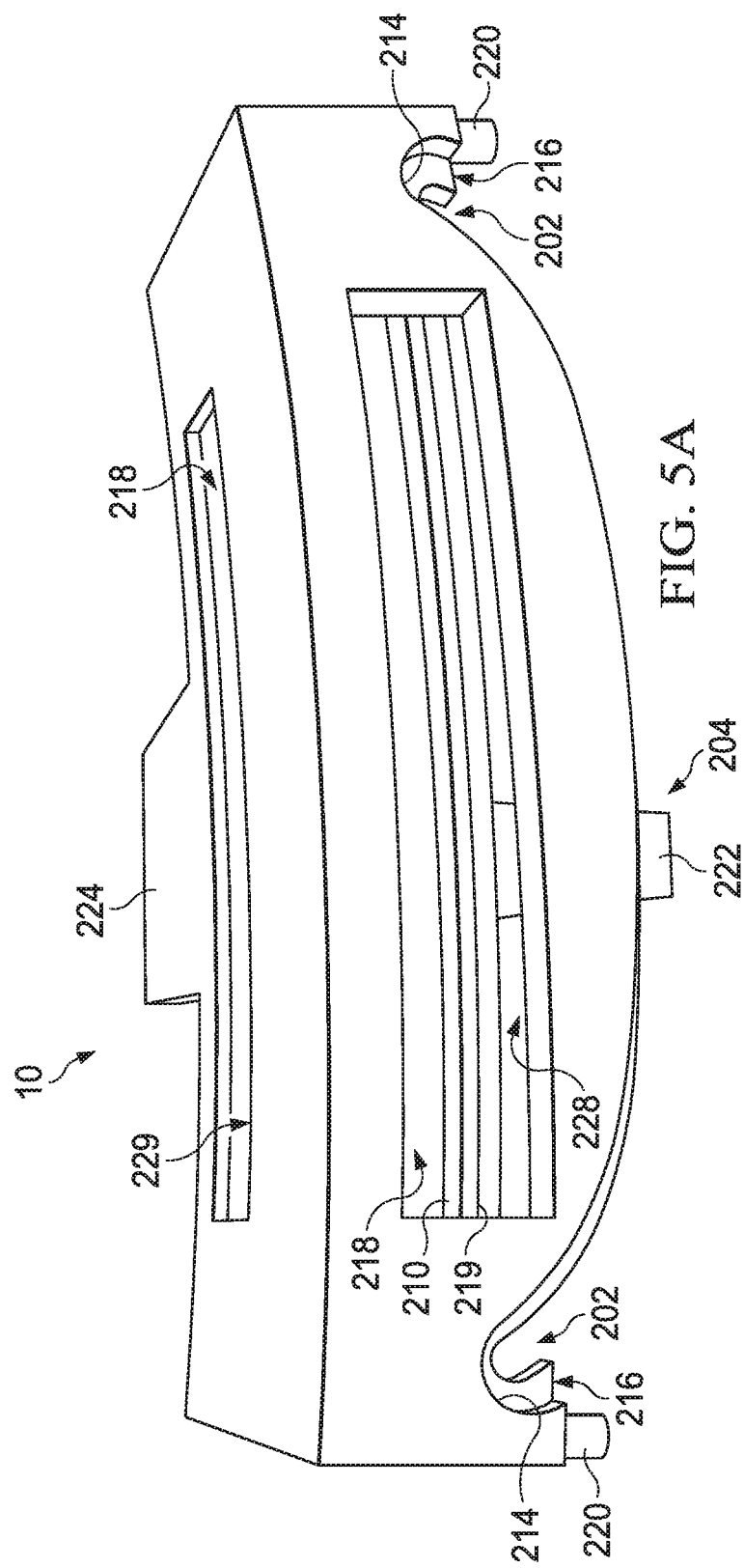

BONE FOUNDATION GUIDE AND METHOD OF USE

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to bone reduction guides. More particularity to those bone reduction guides that could incorporate and support dental implant surgical guide capabilities.

BACKGROUND

As a person ages, they generally incur tooth and bone loss requiring prosthetic replacement as provided by the dental profession. One of the more important aspects of this replacement procedure is the need to solidly anchor within the available bone structure those implants used to secure individual (replacement artificial tooth) or collective (e.g., denture) dental prosthetic. When teeth lose bone around their roots, the bone (e.g., mandibular arch or the maxillary arch) may become uneven (either thinned out or too bulky) in various places in the respective dental arch. This bone condition may make the dental restorative process in that particular area more difficult than when such bone loss has not occurred. It could be thought as building a house/foundation on an unleveled/uneven ground.

In order for the dental prosthetic (or restoration) to be properly fitted to the patient in a substantially esthetically and functionally acceptable position, the dental health care professional (e.g. dental surgeon) may first have to alter the bone of the dental surgical site (especially in those situations where the dental prosthetic is redressing significant tooth loss). This corrective process could start by making one or more incisions in gum area that otherwise designates the dental surgical or restoration site. These incisions substantially allow the gum tissue to be peeled back to expose the bone at the dental surgical site. The dental surgeon, in order to generally make dental surgical site/dental arch symmetrical in all relevant dimensions for the dental restoration (e.g., removable denture) or implant sites (e.g. fixed prosthetics), may then apply one or more cutting tools to generally reduce or remove unwanted high points or thickened places on the exposed bone structure. In other instances, the dental surgeon may add bone material to the exposed bone structure to further fill out the arch's profile or otherwise strengthen its structure.

During this process, the dental surgeon could bring the top portion of the alveolar ridge (e.g., one of the two jaw ridges either on the roof of the mouth or the bottom of the mouth that contain the sockets or alveoli of the teeth) to the correct surgical dimensions ("leveling out") by utilizing a bone reduction guide generally placed upon and secured to the bone structure to guide the cutting/augmenting of the exposed bone. The bone reduction guide solves the problem of "estimating" the vertical height and width of the bone at the "coronal" level by guiding the surgeon's operation of the cutting tools and/or augmentation of the bone. This allows subsequent and accurate placement of the dental implants and respective prosthetics at the proper patient-specific vertical and horizontal levels. This bone adjustment process may also provide for the creation of the proper inter-occlusal room (e.g., the space that exists between the opposing teeth and the open tissue (e.g., that will receive the dental prosthetic) to generally insure that proper jaw operation and alignment, smile line and phonetics occur when the dental prosthetic is finally located within the patient's mouth.

After the exposed bone has been properly been prepared (e.g., reduced/augmented), the bone reduction guide may be removed. A dental implant surgical guide may be subsequently fitted and attached in its place at the remodeled bone of dental surgical site. The dental implant surgical guide may be used to guide the operation of implant accessories needed to prepare the dental surgical site to receive the dental implants. The dental implant surgical guide may then be used to suitably locate the dental implants into the prepared bone structure. After the dental implants are properly located, the dental implant surgical guide may be removed and healing abutments (if required) may be fitted to the dental implants to create a space in the reattached gum proximate to the dental implant(s) that receives a portion (e.g., the base) of prosthetic (e.g., tooth). Once the healing abutments are attached, the gum tissue may sutured back up sand around the dental implant/healing abutment.

As needed, a full upper or full lower denture/tooth may be fitted to the implants either at is the close of the dental surgery or later after healing of the tissues/osseo-integration of bone to implant(s) has occurred. Once the healing/osseo-integration has finalized, the dental surgeon could remove the healing abutments to open up the space proximate to the implants that receives the base of the prosthetic to place and affix the dental prosthetic securely to the implant(s).

The bone reduction guide and the implant dental surgical guide for the implants are generally considered separate instruments that are generally designed, manufactured and used independently of one another other. The design and creation of these guides can be accomplished through digital dentistry (e.g., pre-surgical digital methods and associated apparatuses to obtain and merge medical imaging information taken from the patient's mouth and/or dental castings of the patient's mouth to create a patient-specific virtual models of the preoperative and post-operative mouth and a surgical plan connecting the two models) or manually by dental art and hand (e.g., analogue dental design and preparation).

This separation or compartmentalization of dental guide capabilities could result in higher costs, manpower, and surgical time that could be found than if the two dental guides could be combined into one multipurpose device. The use of such a combination dental appliance could accordingly lead to an increase in the affordability of such dental procedures and results.

What could be needed is a bone foundation guide wherein a bone reduction guide and dental implant surgical guide are formed into a combination as provided by the present invention wherein the dental implant surgical guide directly and reversibly attaches to the body of the bone foundation guide in situ after the open or exposed bone at the dental surgical site has been properly reduced/augmented using the bone foundation guide. The dental implant surgical guide, by attaching directly to or through the bone foundation guide body as anchored, could utilize the bone foundation guide body as a base to generally position the dental implant/implant accessories through the open surgical space to provide proper implant placement relative to the patient's dental surgical site. Additionally, the invention could further comprise of a cutting containment guard that could be removably attached to the bone foundation guide body to provide a combination of guard and body that forms a cutting slot that could accept a cutting edge (e.g., blade) of cutting implement to subsequently guide the movement of the cutting implement and blade with greater precision in bone removal at a dental surgical site.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide an dental implant surgical guide that is reversibly combines with bone foundation guide body to consequentially properly place a dental implant-retained prosthesis in a manner that reduces patient stress and bruising that may occur if the two guides were applied separately;

the ability to use a digital virtual model of patent mouth to design a bone foundation guide body and a dental implant surgical guide to consequentially conjoin both body and guide to properly locate that locates and secures a fixed dental prosthetic at a dental surgical site where exposed bine had been altered;

to provide dental implant surgical guide/bone foundation guide body combination to reduce cost, time and man-hours needed in a surgical procedure to properly locate and attach a fixed prosthetic to a dental surgical site;

the ability to use digital dentistry to control the design and manufacture of a dental implant surgical guide/a bone foundation guide combination to digitally control refine the accuracy of the bone foundation guide; dental implant surgical guide; and final fixed prosthetic; and to provide a tissue spacer guide that can working in conjunction with combined bone foundation guide/dental implant surgical guide to adjust for the height of gum tissue that would normally cover the bone at the dental surgical site;

the ability to design and manufacture a dental surgical guide, bone foundation guide, and tissue spacing gasket to allow them to mate together and allow implant appliances and implants to pass through the combination onto the bone at a dental surgical guide;

to provide a cutting containment guard that attaches to the bone foundation guide body to provide a side located cutting slot that accepts a cutting edge of a cutting implement to guide a cutting of an exposed bone from a dental surgical site with greater precision by limiting the ability of the cutting edge from jumping off of the body;

the ability to hold a cutting implement in a proper moving relationship with the body of the bone foundation guide to make a more efficient cut of the bone that is to be removed from to the patient's mouth;

the ability to remove with a single cut a segment of bone from the patient's mouth to allow the bone be re-used as an autologous bone filler to augment the bone of the dental surgical site;

to provide a cutting containment guide that provides a backstop to the cutting implement as well as holds down the cutting implement down upon the top of the body of the bone foundation guide;

the ability to further guide the cutting implement moving a non-cutting portion of the cutting implement into and along a tool channel that generally matches the placement of the cutting slot of the cutting containment guard;

to provide a cutting containment guard that has end positions for the cutting channel that generally permit the implement to engage and disengage from the dental surgical site without having direct contact with the bone of the dental surgical site; and to provide a dental surgical guide, bone foundation guide, and tissue spacing gasket to have matching contours and aligned openings and apertures that allow guides and gasket to be combined into one operating unit to properly locate and attach a fixed prosthetic to a dental surgical site.

These and other advantages may be realized by reference to the remaining portions of the specification, claims, and abstract.

BRIEF DESCRIPTION OF ONE EMBODIMENT OF THE PRESENT INVENTION

One possible embodiment of the invention could be a bone foundation guide comprising: a bone foundation guide body for guiding a reshaping of an exposed bone at a dental surgical site, the bone foundation guide body having a buccal wall and a lingual wall that is continuously connected by a first end and a second end to form an encircled open surgical space that continuously connects a top and a bottom of the bone foundation guide body, the top being contoured to guide a cutting implement to reshape the exposed bone; a cutting containment guard that attaches to the top to form a combination of body and cutting containment guard, the combination forming a cutting slot that receives and guides a cutting edge of the cutting implement used to reshape the exposed bone at the dental surgical site, the cutting containment guard being removed from the body after the exposed bone is reshaped; a dental implant surgical guide that attaches to the body in place of cutting containment guide to direct the placement of one or more implants through the encircled open surgical space; wherein the bottom is contoured to reversibly affix to the exposed bone while the top can removably accept the cutting containment guard or in alternative the dental implant surgical guide.

Another possible embodiment could be a bone foundation guide comprising a bone foundation guide comprising a bone foundation guide body contoured to guide a cutting implement to alter an exposed bone of a dental surgical site, the bone foundation guide body comprising of a buccal wall and a lingual wall held apart from each another by a first end and second end in a manner that denotes an encircled open surgical space continuously connecting a top and a bottom of the bone foundation guide body, the encircled open surgical space capable of passing one or more dental implants through the bone foundation guide body to the dental surgical site, the bottom is further contoured to affix to the exposed bone of the dental surgical site while the top is further adapted to support a dental implant surgical guide or in the alternative a cutting containment guard; and the cutting containment guard having a cutting channel for receiving the exposed bone when the cutting containment guard is combined with the bone foundation guide body, the combination forms a cutting slot for guiding a cutting edge of a cutting implement to alter the exposed bone from the dental implant surgical guide.

Yet another possible embodiment of the invention could be a method of using a bone foundation guide comprising the following steps, but not necessarily in the order shown: providing a bone foundation guide body having a top and a bottom, bone foundation guide body further forming an encircled open surgical space, the bottom is further contoured to receive and rest upon an exposed bone of a dental surgical site while the top is contoured to guide the alteration of the exposed bone of a dental implant surgical site by a cutting implement, the top is further capable of reversibly receiving and supporting a cutting containment guard and in the alternative a dental implant surgical guide; providing a cutting containment guard that when combined with the bone foundation guide body forms a cutting slot that accepts a cutting edge of the cutting implement; removably anchoring the bone foundation guide body upon the exposed bone; and combining the bone foundation guide body and cutting containment guard to form a cutting slot; and altering the exposed bone by inserting the cutting edge of the cutting implement into the cutting slot.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 5A is substantially a perspective cutaway view of one embodiment of cutting containment guard.

DESCRIPTION OF CERTAIN EMBODIMENTS OF THE PRESENT INVENTION

Figure 1:
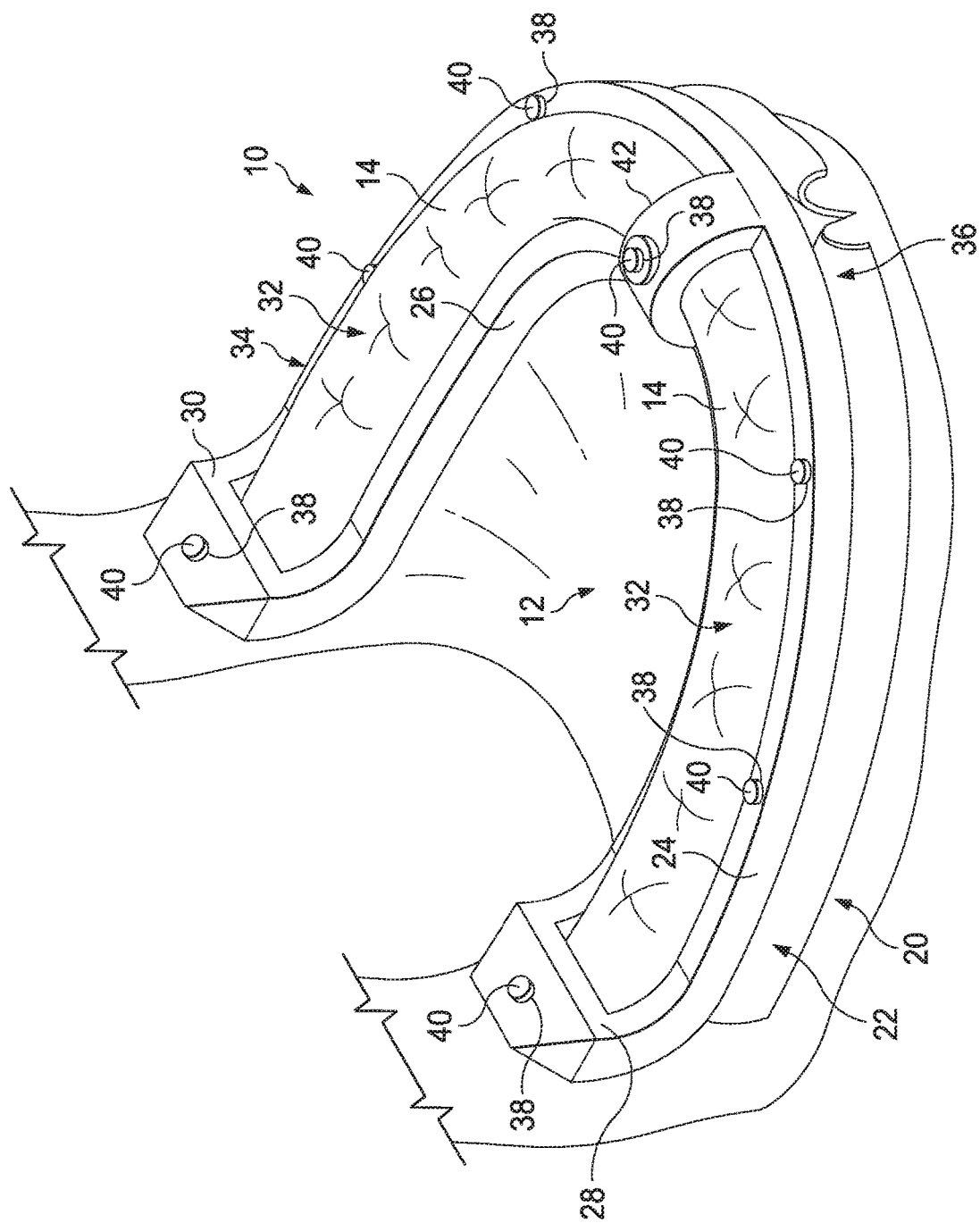
FIG. 1 is substantially a perspective view of one possible embodiment of the bone foundation guide the invention applied to an alveolar ridge.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The present invention 10 could comprise of bone foundation guide 20 that can accommodate and support a dental implant surgical guide 50 and a respective method or process of such use 100. Both the bone foundation guide body 22 and the dental implant surgical guide 50 may be designed and created together through digital dentistry in which scans of patient's mouth (along with impressions and castings thereof) may be used to create a virtual model of the patient's existing mouth; to develop a virtual model of the patient's mouth both pre-dental and post-dental surgery; and to develop a dental surgical plan that connects the two patient-specific virtual models. In this manner, the dental surgical planning can provide for the manufacture of the two respective guides so that the contours of the bone foundation guide body 22 may be created to fit upon the bone 14 of the dental surgical site 12 and as well as properly interact with the contours of the dental implant surgical guide 50 enabling the dental implant surgical guide 50 to fit upon the bone foundation guide body 22.

Figure 2:
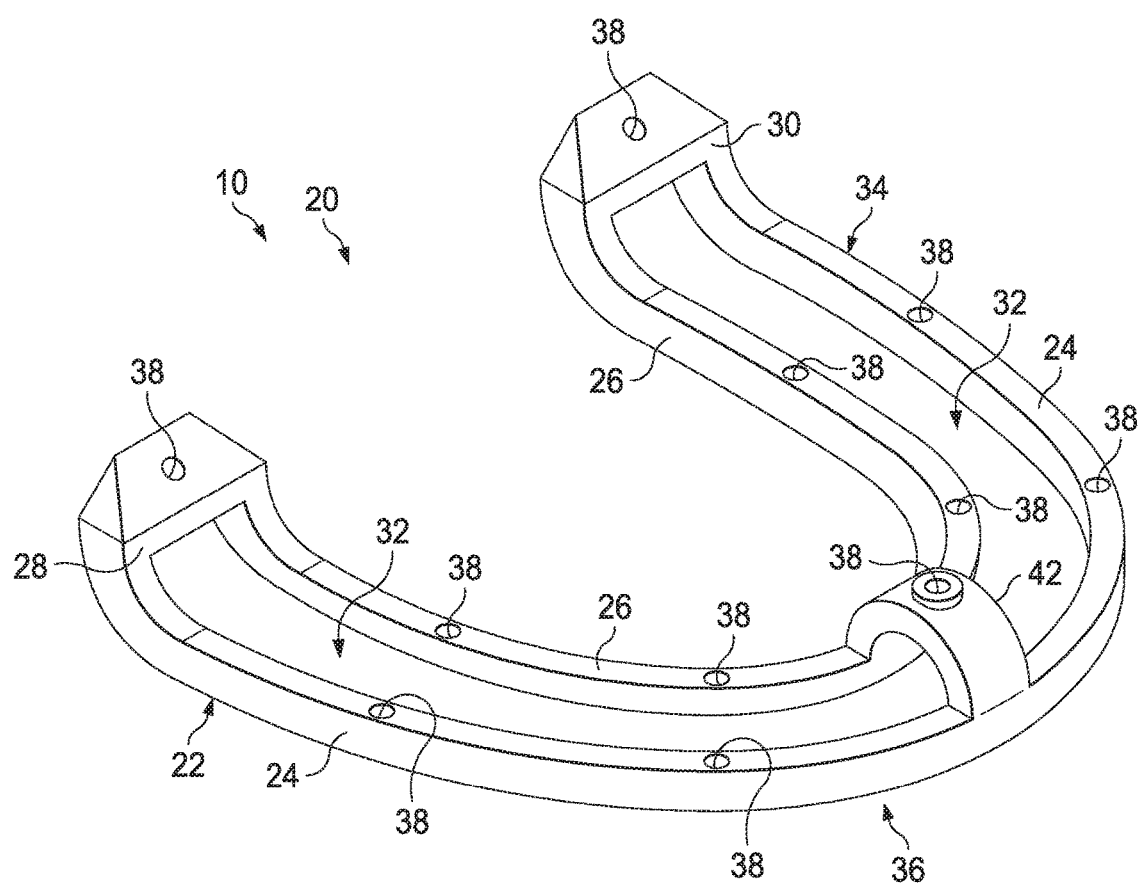
FIG. 2 is a perspective view of one possible embodiment of bone foundation guide of the present invention.

As substantially shown in FIGS. 1 and 2, the bone foundation guide 20, as substantially used by a dental surgeon (not shown) to substantially reduce or augment an exposed bone structure of the dental surgical site 12 as needed for a successful dental surgery, could comprise a bone foundation guide body 22 with a buccal wall 24 and lingual wall 26 connected together at their respective ends by a first end 28 and a second end 30. The first end 28 and the second end 30 could be holding the walls 24, 26 apart from one and other, in a substantially parallel fashion, to generally create and define an encircled open surgical space 32 (e.g., formed by the bone foundation guide body 22 and generally passing through the bone foundation guide body 22 to generally continuously connect a portion of the top 34 with a portion of the bottom 36). The top 34 could be contoured to guide a cutting implement 300 to reshape an exposed bone 14 of a dental surgical site 12 (as substantially shown in FIG. 2A.)

The bone foundation guide body 22 may be further penetrated by one or more attachment apertures 38 to generally continuously connect the top 34 and bottom 36, although in some embodiments the attachment apertures 38 may be oriented to pass through a buccal 24 wall and/or lingual wall 26. Fasteners 40 may pass through the attachment apertures 38 to substantially anchor into the bone 14 of the dental surgical site 12 (e.g., alveolar ridge) to reversible secure the bone foundation guide body 22 to dental surgical site 12. The attachment aperture 38 could further feature a reinforcement collar (not shown) to support and guide the is fastener 40 through the attachment aperture 38.

In some embodiments, the bone foundation guide body 22 may further comprise of a bridge 42 that connects the buccal wall 24 with the lingual wall 26 between the first end 38 and the second end 30 and effectively bisecting the open surgical space 32 in some versions of the embodiment. The bridge 42 in such embodiments may also have an attachment aperture 38 penetrating it as well. After the bone foundation guide is secured to the dental surgical site 12, in some versions of the invention 10, the bridge 42 could be removed (e.g., be cutout) if needed.

Figure 2A:
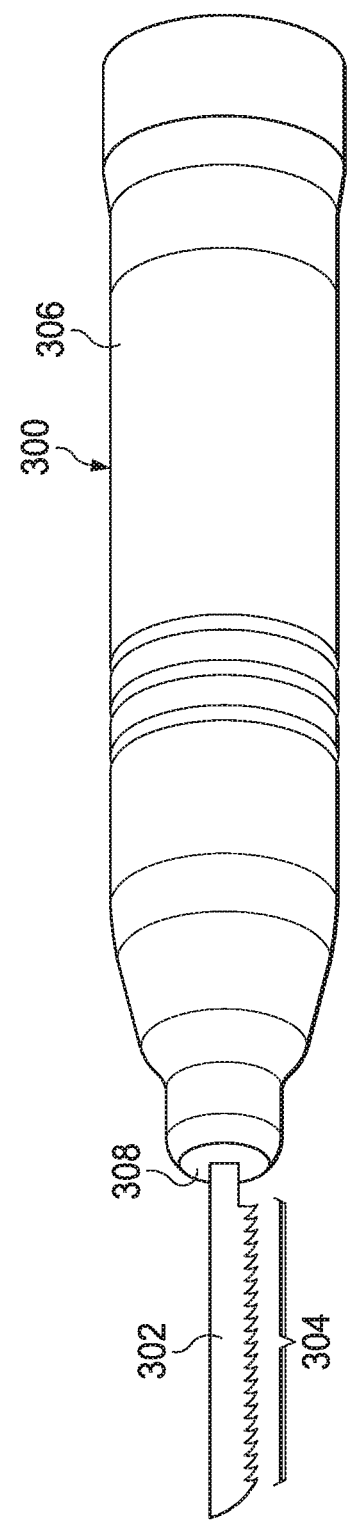
FIG. 2A is a perspective view of one possible embodiment of a cutting implement.

As substantially show in FIG. 2A, the bone foundation guide 20 could interact with a cutting implement 300 such as a bone saw (e.g., reciprocating, oscillating, sagittal, etc.) Such a cutting implement 300 could comprise of an motor (not shown) contained within a body 306 that can be held by a dental health care professional as needed to generally manipulate and move the cutting implement 300. The motor could be further connected to a blade 302 (e.g., a saw blade) through the tip 308 of the body 308, the motor substantially providing appropriate cutting motion to the blade 302. The cutting edge 304 of the blade 302 could be serrated (e.g., for a saw blade) and be brought into contact with the exposed bone 14 as guided by the surface of the top 34 of the bone foundation guide 20 (substantially shown in FIGS. 1 and 2). If the blade 302 has serrated edge, the teeth of the serrated edge near tip of the blade 302 could be removed or otherwise masked to prevent the blade 302 from otherwise cutting into a backstop 218 or a backstop shelve 219 (substantially shown in FIG. 5C) as the moving blade engages the bone foundation guide and moves relative to the backstop and backstop shelve 219.

Figure 3:
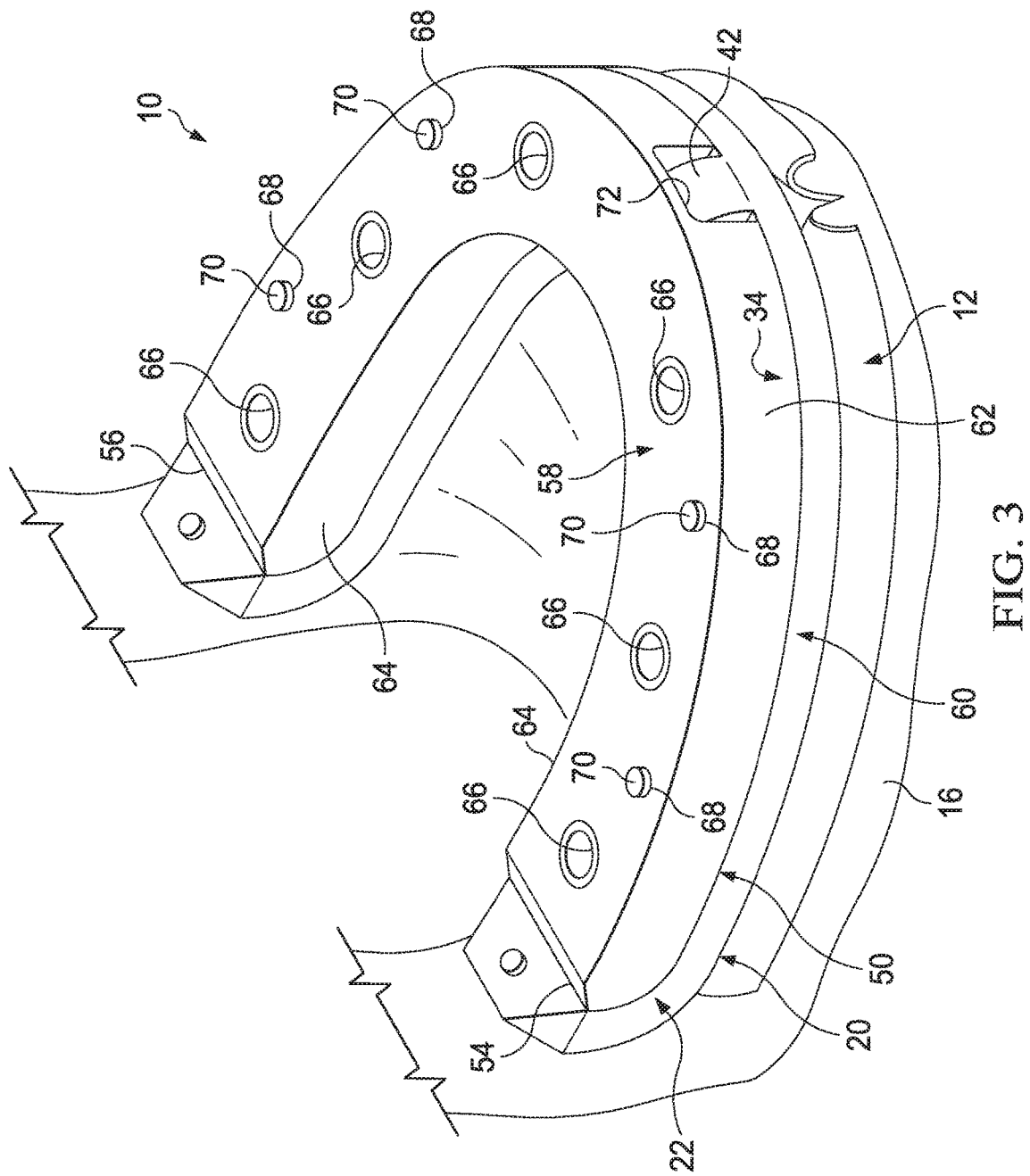
FIG. 3 is substantially a cutaway perspective view of one possible embodiment of the dental implant surgical guide applied to the bone foundation guide.
Figure 4:
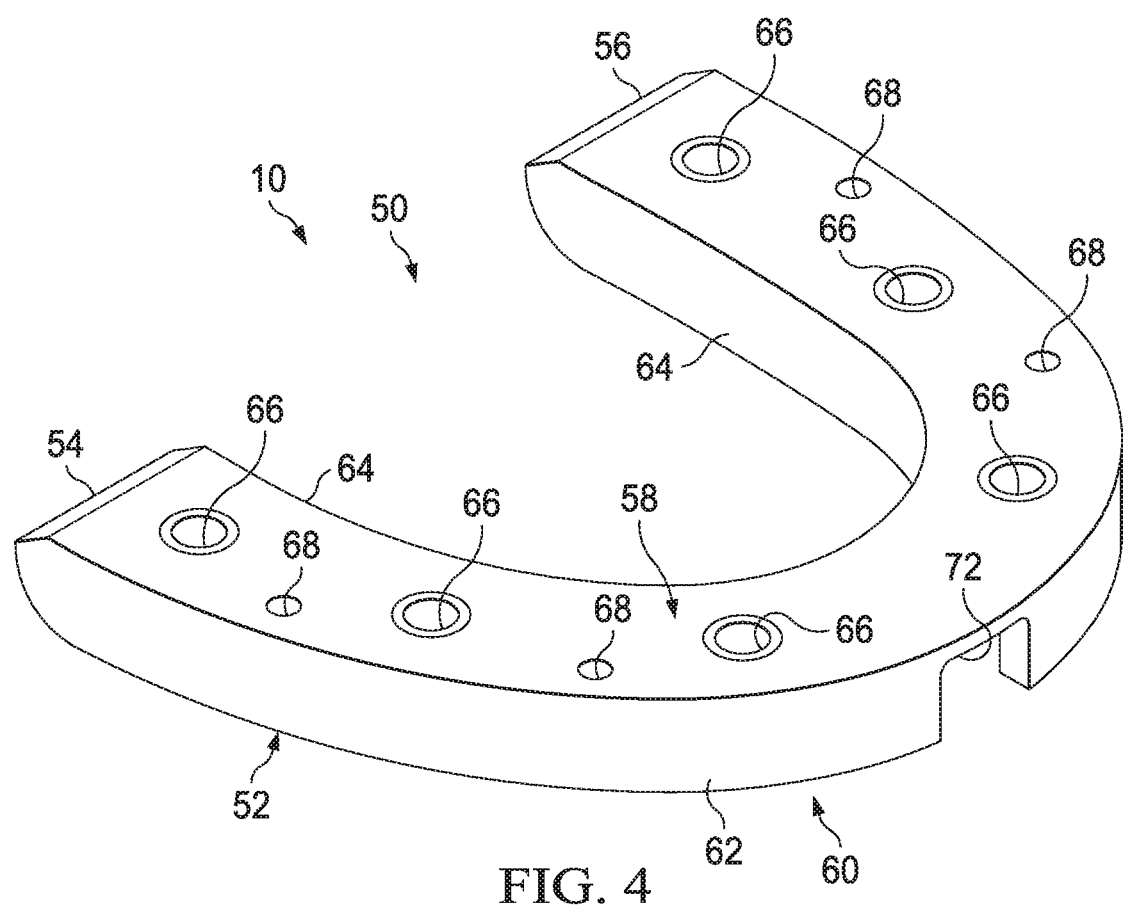
FIG. 4 is substantially a perspective view of one embodiment of the dental implant surgical guide.

As substantially shown in FIGS. 3 and 4, the dental implant surgical guide 50 could be generally used to guide and locate the placement of dental implants in the dental surgical site 12. The dental implant surgical guide 50 could comprise a dental surgical guide body 52 having a first end side 52 and second end side 54 that terminates the dental surgical guide body 52 and along with a top side 58 and a bottom side 60 that continuously connect a buccal side 62 with a lingual side 64. The bottom side 69 could be designed and/or contoured to removably receive the top 34 of the bone foundation guide 20 to generally allow the dental implant surgical guide 50 to be combined with and attached to the bone foundation guide 20.

The dental surgical guide body 52 can be further penetrated by implant apertures 66 that could continuously connect the top side 58 to the bottom side 60 to guide implant preparation and attachment to the dental operation site 12. The dental surgical guide body 52 could additionally have fastener apertures 68 penetrating the dental surgical guide body 52. The fastener apertures 68 may align up with the respective attachment apertures 38 on the bone foundation guide body 22 so that an extended fastener 70 may pass through both the dental surgical guide 50 and the bone foundation guide 20 to attach to the bone 14 relative to the dental surgical site to combine the two guides 20, 50 in place at the dental surgical site 12. In other embodiments, the fastener apertures 68 may align up with respective receptacles in the bone foundation guide body 22 to allow the fasteners 40 passing through the dental surgical guide 20 to anchor into the bone foundation guide body 22 to combine the bone foundation guide 20 with the dental implant guide 50. In this manner, the dental implant surgical guide 50 could attach directly to the dental surgical site 12; attach to the dental surgical site 12 through the bone foundation guide 20; attach to just the bone foundation guide 20, or combinations thereof.

The bottom side 60 of the dental implant surgical guide 50 can be digitally designed/manufactured to have a contour (e.g., top side 58) that substantially matches the top 34 of the bone foundation guide 20. Conversely, or conjointly, the top 34 of the bone foundation guide body 22 may be digitally designed and created to substantially match and to receive the bottom side 60 of the reciprocal dental surgical guide body 52 to allow the dental implant surgical guide 50 to be mounted to the bone foundation guide 20 so that the bone foundation guide 20 can be joined with the dental implant guide 50 to act as a base for the dental implant surgical guide 50. This conjoining of guides 20, 50 could alleviate the need to remove the bone foundation guide 20 from the dental surgical site 12 prior to attaching the dental implant surgical guide 50 to the dental surgical site 12 as well as alleviate the need to attach the dental implant surgical guide 50 directly to the dental surgical site 12 and the like. In this manner, the dental implant surgical guide 50 generally encloses the open surgical space 32 to allow implants/implant accessories (e.g., implant preparation tools)(not shown) passing though the dental implant surgical guide 50 to be generally pass through an open surgical space 32 of the bone foundation guide 20.

In one possible embodiment, the bottom side 60 of the dental implant surgical guide 50 could have a recess 72 that could accommodate the bone foundation guide's bridge 42. If the bridge 42 was penetrated by an attachment aperture 38, the dental implant surgical guide body 52 could have a respective fastener aperture 68 that could align together to allow passage of the extended fastener 70. Similarly, if an implant aperture 66 penetrated the recess 72 then a suitable aperture or channel could penetrate the bridge 42 to allow implant preparation and attachments to penetrate the bridge 72 as well. In another possible embodiment, the bridge 72 could be cut and removed from the bone foundation guide body 22 so that any implant/implant preparation (e.g., drills, reamers, etc.) could pass unimpeded through that opened-up portion of the an open surgical space 32.

Figure 5:
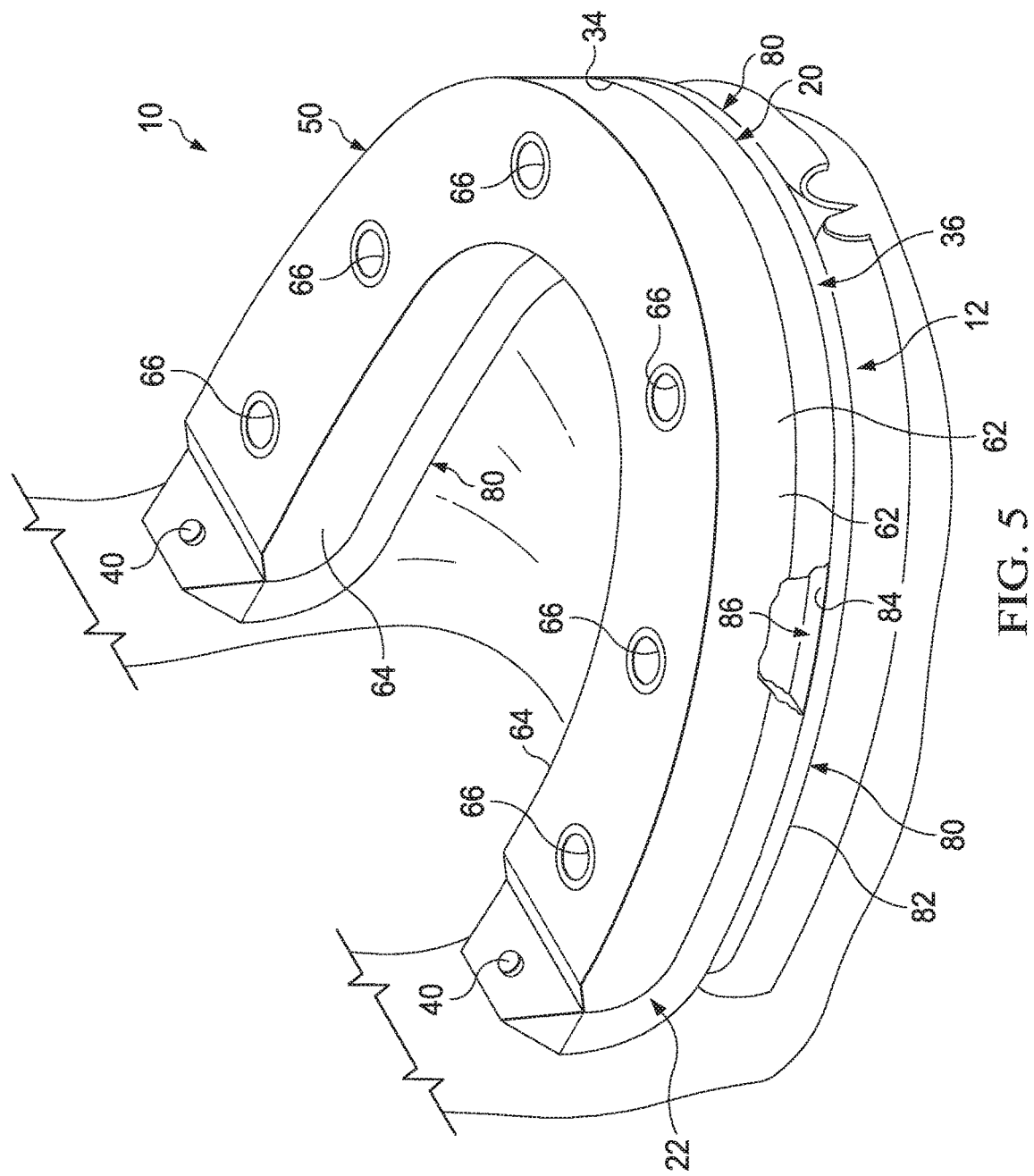
FIG. 5 is substantially a perspective cutaway view of one embodiment of the tissue spacing gasket.
Figure 5B:
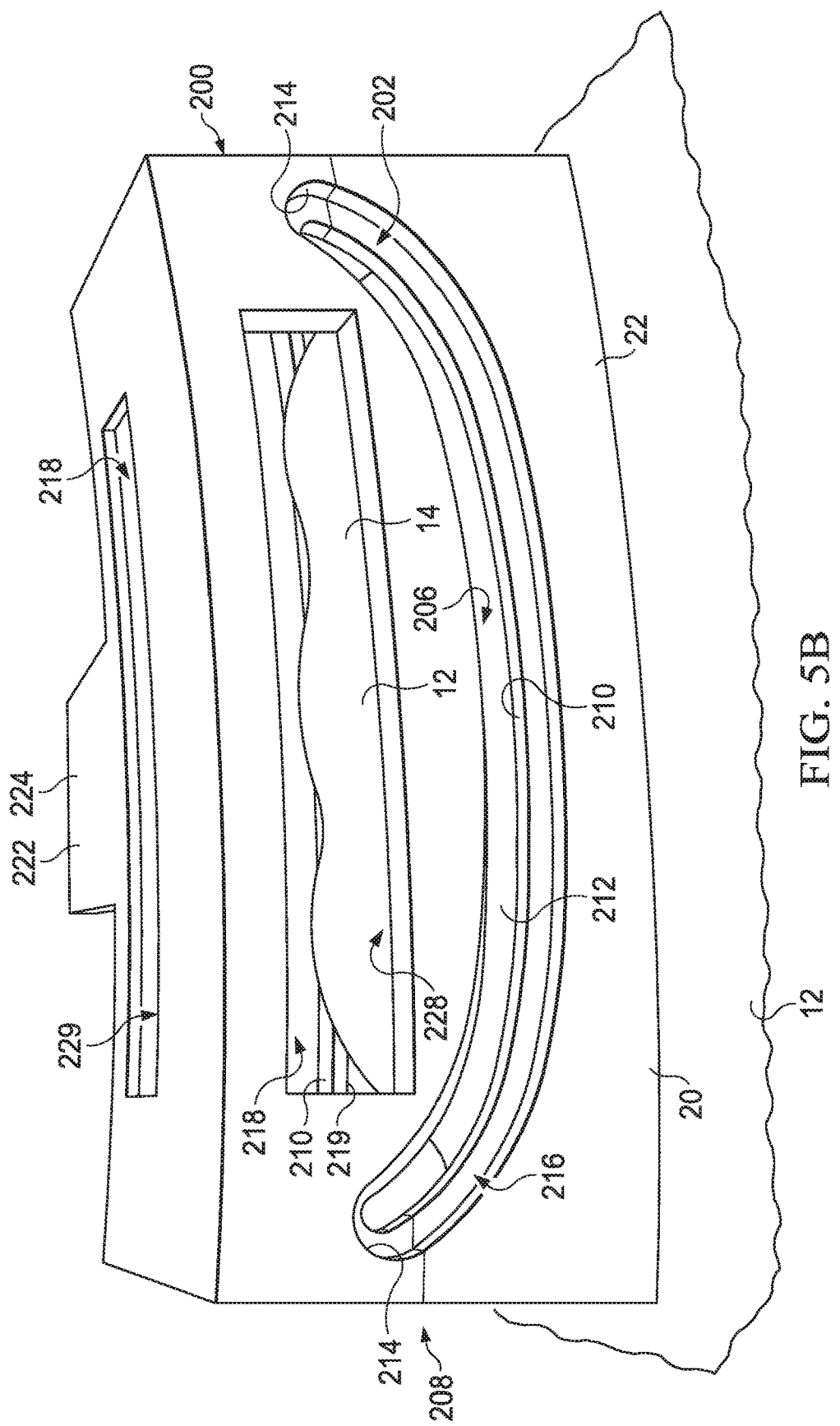
FIG. 5B is substantially a perspective cutaway view of one embodiment of cutting containment guard combined with the body of the bone foundation guide.

As substantially shown in FIG. 5, one other possible embodiment of the invention 10 could further comprise a tissue spacing gasket 80 that fits between the dental surgical site 12 and the bottom 36 of the bone foundation guide 20. The tissue spacing gasket 80 could be used to set apart the bottom 36 of the bone foundation guide from the dental surgical site 12 to properly replicate the positioning of the dental implant surgical guide 50 (as placed on top 34 of the bone foundation guide 20) as if the gum tissue 16 had been reattached to the surgical (bared bone) site. The thickness of the tissue spacing gasket 80 could be set to the thickness of the gum 16 at that dental surgical site 12 while the gasket bottom 82 can be designed/manufactured to have a contour that matches that of the dental surgical site 12 while the gasket top 84 is contoured to match the bottom 36 of the bone foundation guide 20. The tissue spacing gasket 80 could be designed and constructed to have own matching gasket open surgical space that could generally match the footprint of open surgical space 32 of the bone foundation guide 20. Alternatively, the tissue spacing gasket 80 could have individual gasket apertures (not shown) that could be in alignment with the dental implant surgical guide's implant apertures 66. Other versions of the tissue spacing gasket 80 could have additional apertures (not shown) as needed to be in alignment with any fastener apertures/attachment apertures as needed.

Figure 5C:
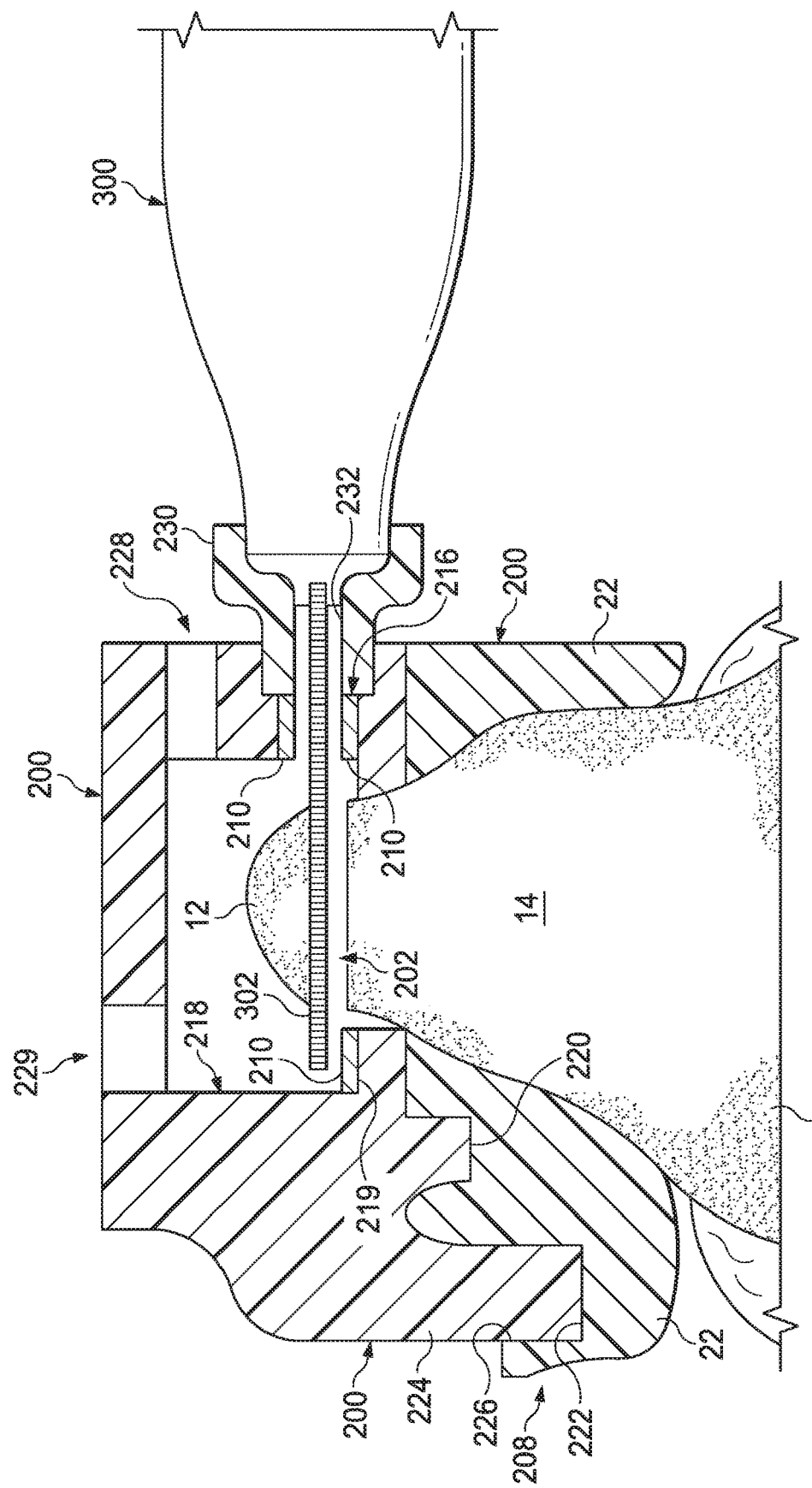
FIG. 5C is substantially an end elevation cutaway view of one embodiment of cutting containment guard combined with the body of the bone foundation guide.
Figure 5D:
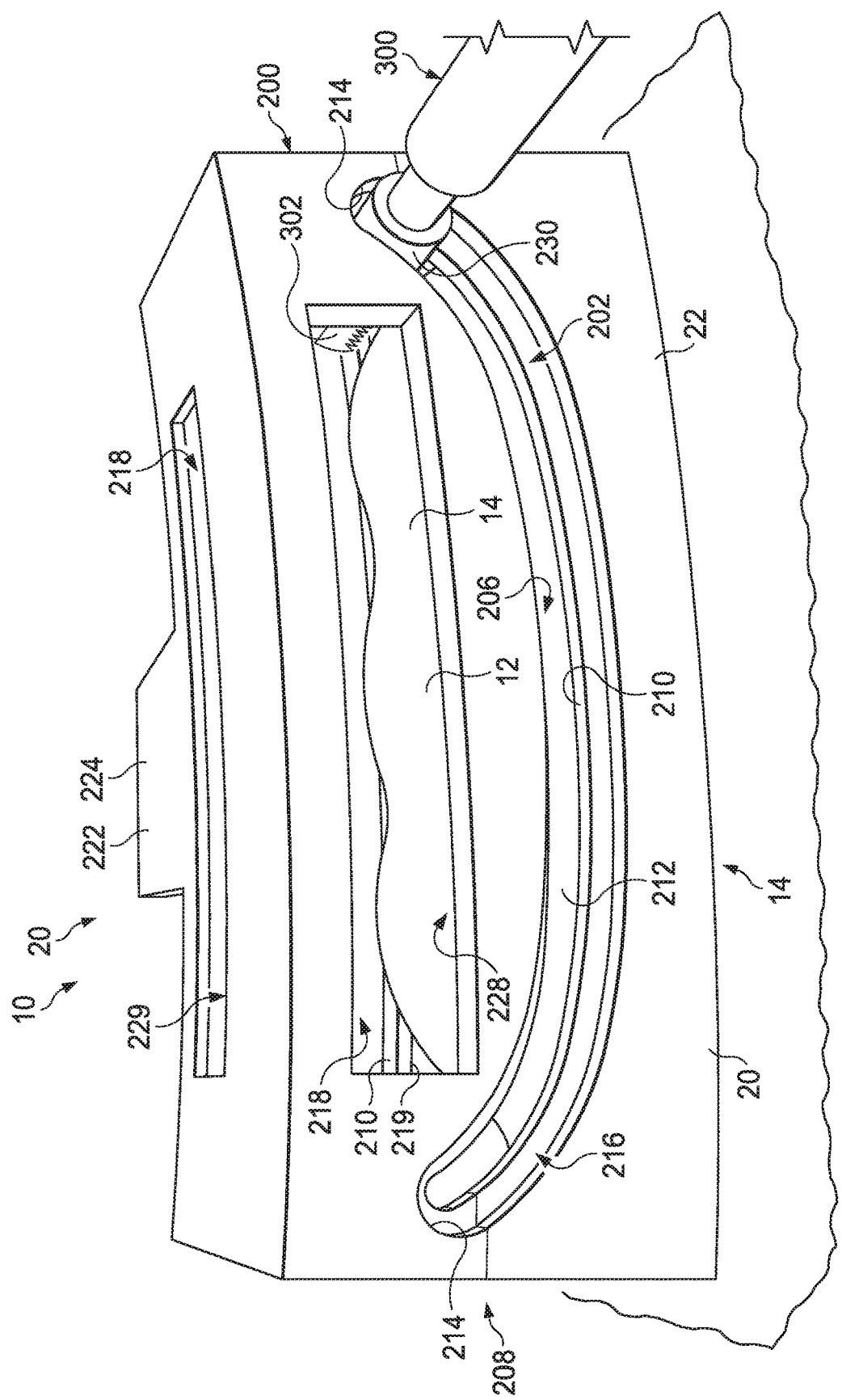
FIG. 5D is substantially a perspective cutaway view of one embodiment of cutting containment guard combined with the body of the bone foundation guide being engaged by a cutting implement.

As substantially shown in FIGS. 5A, 5B, 5C and 5D, the invention 10 could further comprise a cutting containment guard 200 that once combined with the body 22 of the bone foundation guide 20 generally provides a cover over the top 34 of the body 22 that generally creates a side-located or transversely presented (e.g., transverse to the open surgical space 32) cutting slot 202. The cutting slot 202 substantially directs and limits the action and movement of a cutting edge 302 (e.g., of reciprocally moving saw blade 302) of a cutting implement 300 (e.g., bone saw) that is inserted along a transverse path (e.g., transverse to the open surgical space 32) into the cutting slot 202 as shown in FIG. 5C and used to cut a portion of a bone 14 of the dental surgical site 12 upon which the body 22 is located. The guard bottom 204 could have a cutting indention or channel 206 that opens both to a buccal side and the guard bottom 204. This cutting channel 206 could suitable be constructed (e.g., having sufficient depth and contour) to substantially accommodate that portion of exposed bone 14 that is to be cut free from the dental surgical site 12. When the cutting containment guard 200 is generally combined with the top 34 of the body 22, the resulting combination 208 could form the cutting slot 202. If the cutting containment guard 200 and the body 22 are made of a soft material such as a plastic polymer, then strips of metal (such as titanium, surgical stainless steel and the like) can be affixed to the top and bottom of the cutting slot 202 (e.g., top 34 of the body 22, the guard bottom 204) to create rails 210 that can guide the cutting edge 302 within the cutting slot 202 in a manner that prevents the cutting edge 302 from damaging the top 34 of the body 22 and the guard bottom 204.

In at least one embodiment of the invention 10, the cutting containment guard could comprise of one or more viewing ports to observe the interaction of the cutting implement 300, the exposed bone 14 of the dental surgical site 12 and the combination 208 of the body of the bone foundation guide and the cutting containment guard. One such view port could be a top port 229 located towards the back of the cutting containment guard 200 which could allow observation of blade 302 operating on top of the rail 210 proximate the backstop 218. In this manner, the operator (not shown) could watch and hold the tip of the blade 302 upon that railing 110 to generally make sure that the cut is being made upon the exposed bone is substantially even and horizontal (e.g., to substantially reduce bone wastage and increase bone harvesting possibilities.) Another view port could be a front port 228 generally located above the cutting slot to allow the operator (not shown) to peer into cutting channel 206 to see how well the exposed bone is being cut by the cutting implement 300.

The formed cutting slot 202 could comprise a cutting portion 212 that continuously connects a two non-cutting ends 214. The non-cutting ends 214 could be used to insert cutting edge 304 into or remove the cutting edge 304 from the combination 208 without having the cutting edge 302 contact the exposed bone 14. At the start of the cutting, the cutting edge 302 could be loaded into a suitable non-cutting end 214; be brought up to operating speed and then guided in a controllable manner by the cutting portion 212 of the cutting slot 22 to be brought into contact with the exposed bone 14. As the cutting portion 212 is used to move the cutting edge 300 through exposed bone 14, the cutting edge 300 can then stop at the other non-cutting end 214 where the cutting implement 302 can be de-powered to allow the movement of the cutting edge 300 out of contact with exposed bone 14. This blade positioning could allow for the safe and controlled withdrawal of the cutting edge 300 from the combination 208.

In one embodiment of the invention, the width of the formed cutting slot (distance between the guard bottom 204 and top 34 of the body 22) could be enough to accommodate the thickness of the cutting edge 300 (while under cutting movement) but not tight enough to cause binding of the moving cutting edge 300. In another embodiment using the backstop shelf 219 as a counter point to the blade contact as held between the cutting slot 202, the width of the cutting slot could be wider. In either manner, the cutting slot width could prevent the cutting edge 300 from bouncing off the top 34 of the body 22 during bone cutting and removal operations, thus further preventing an inefficient bone cut that may require supplemental cutting to remove all the desired exposed bone. This greater efficiency in bone cutting or harvesting could further provide for greater recapturement of the harvested bone 14 allowing the harvested bone 14 to be more efficiently used as autologous bone filler to augment the bone of the dental surgical site.

In one version of the invention 10, the body and guard combination 208 of could further form a tool side channel 216 that generally overlays the cutting slot 202 on the buccal side of the combination 208. The tool side channel 216 could removably accept a portion of the body cutting implement's body 306 such as the tip 308. In this manner, as the cutting edge 300 is moved into the cutting slot 202, the cutting implement 302 (e.g., tip 308) could be moved into and be accommodated by the tool side channel 216. As the cutting slot 202 guides the cutting movement of the cutting edge 300; the tool side channel 216 could help guide the associated movement of the cutting implement 302 by being movably abutted against the buccal side of the combination 208. This dual contact capability could further aid in the preventing the binding of the cutting edge 300 within the combination 208 by keeping the cutting implement 302 and cutting edge 300 aligned with one another as the cutting edge 300 is moved through the cutting slot 22. This dual contact capability could possible help control the depth of penetration by the saw blade 302 within the combination of the bone foundation guide 20 and cutting containment guard 200. Controlling the depth of penetration in this manner could prevent the saw blade 302 from cutting into the backstop 213.

The back (e.g. lingual side) and ends of the cutting channel could further define the back stop (e.g., backside) 218 and terminal ends 220 of the cutting slot 202 when in combination 208 with the top 34 of the body 22. The back stop 218 could (along with the tool side channel 216) limit how far cutting edge 300 could protrude lingually into dental surgical site 12 to substantially prevent the damaging of the tongue, plates and like (e.g., non-dental surgical site portions of the patient's mouth) by the cutting implement 300. The backstop 118 could further form a backstop shelf 219 upon which the tip of the saw blade 302 could ride upon as the saw blade 302 is moving through the bone foundation guide 20. By having the blade 302 riding upon the backstop shelf 219 and cutting channel (e.g., rails 210) the invention 10 could provide a multi-point blade contact for increased precision guidance of the bone altering action by the cutting implement 300. Similarly, the non-cutting 214) could prevent unwanted cutting on arch as it borders the ends of the dental surgical site 12.

In one version, the combination 208 could be removably held together by sets of connection points 220 in a manner that prevents the cutting containment guard 200 from tilting out of place when in the combination in a manner that could otherwise cause an unwantedly narrow or close-off the cutting slot 202 during cutting operations. One such sets of connection points 220 (e.g., slot and pin connectors) could be located on respective ends (e.g., the guard bottom 204 and top 34 of body 22) of the combination 208 to generally prevent the cutting containment guard 200 from sliding over the body 22. A back connection point 222 (e.g., a tab and slot connector) could comprise of a rear extension 224 protruding from the back (e.g., lingual side) of the cutting containment guard that drops into and removably locks into a receiving slot 226 at the lingual wall 26 of the body 22. The back connection point 222 could rely upon a friction fit to hold rear extension 224 together with the receiving slot 226. When the bone cutting or harvesting is completed, the back connection point 222 can be disassociated to allow the removal of the cutting containment guard 200 from the body 22 so that the dental implant surgical guide could be affixed to the body 22.

Figure 5E:
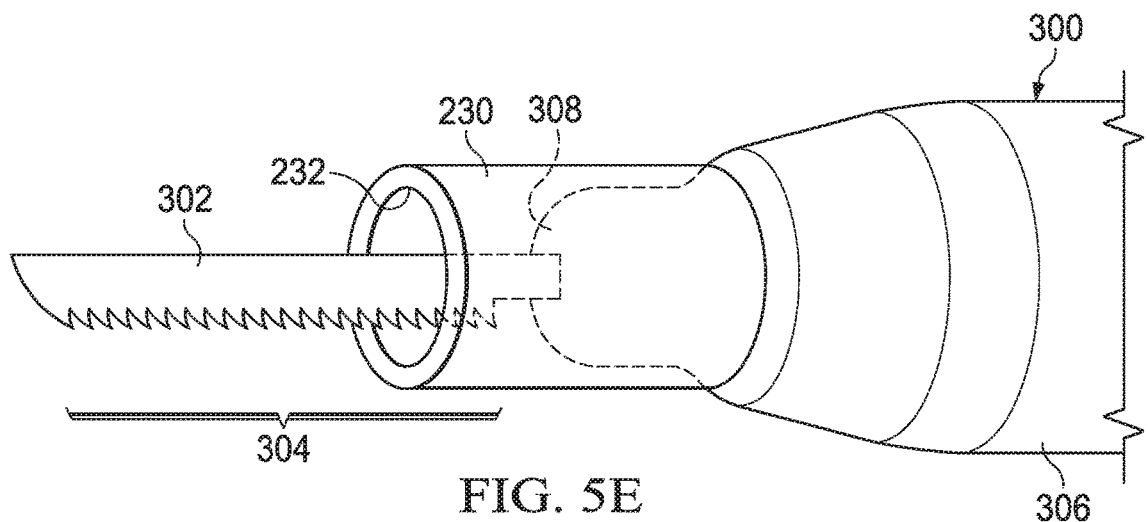
FIG. 5E is substantially a perspective cutaway view of one embodiment of tip guard.

In another possible embodiment, as substantially shown FIGS. 5C and 5E, the invention 10 could further comprise a cup-shaped guide tip 230 having a blade aperture 232 in the guide base 234 of the guide tip 230. The guide tip 230 could be shaped to removably attach to the tip 308 of the cutting implement 300. The guide tip 230 could hold onto the tip 308 through a friction fit. The blade 302, as generally attached to the cutting implement 300, could pass through the interior of the guide tip 230 and exit out the blade aperture 232. The guide base could constructed to movably fit flush within the tool side channel 216 to provide a better and more controlled mating of the cutting implement 300 to the combination 208. In this manner, by holding the cutting implement 300 with guide tip 230 into the cutting channel 212 and then moving the cutting implement 300 along the cutting slot 202, the cutting implement 300 interface as provide guide tip could more closely align the movement of cutting implement 300 with contours of the cutting slot generally increasing the precision of the cut through the exposed bone 14 as provided by the invention 10.

Figure 6:
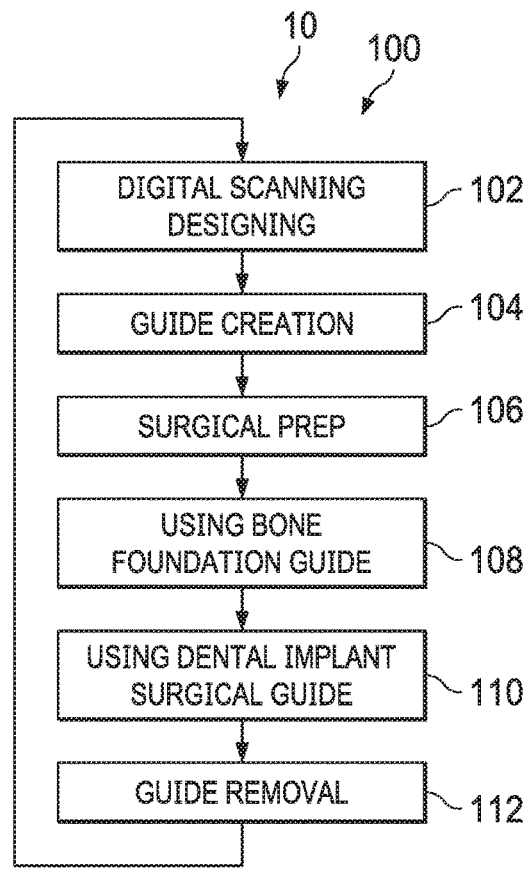
FIG. 6 is substantially a flow schematic showing a method of using the invention.

As substantially shown in FIG. 6, one possible method or process 100 for the use of the invention could start with step 102, digital scanning and modeling for the patient-specific dental surgery. In this step, dental digital methods (digital dentistry) may be used in creating patient-specific map of the patient's mouth (which could include the digital scanning of analogue appliances such as patient specific castings and impressions); in creating models for patient-specific bone remodeling (e.g., foundation and re-contouring) of the upper and/or lower dental arches in the patient's mouth; in creating models for dental implant surgical guides/bone foundation guides, cutting containment guards and prosthetics using post-patient-specific bone remodeling; in creating a patient specific model of the patient's mouth post dental surgery. After this step is substantially completed, the process 100 could proceed to step 104, creation of the guides and other dental appliances.

In step 104, creation of the guides and other dental appliances, the acquired and processed modeling data can be used to create the patient-specific bone foundation guide, cutting containment guard and patient-specific dental implant surgical guide that can work in combination as one unit. In this manner, the contours of the bottom side of the dental implant surgical guide can be substantially designed and manufactured generally match the top of the bone foundation guide to allow the two guides to mate together. This mating capability could allow the two guides to come together to form a single apparatus to generally create a dental implant surgical guide that could attach to the bone foundation guide (e.g., as already secured to the dental surgical site). This kind of mating could also be provided for the bone foundation guide and the cutting containment guard. This ability could allow the implant/implant apparatuses being guided through the dental implant surgical guide/the open surgical space to properly interact with the dental surgical site. After this step is substantially completed, the process 100 could proceed to step 206, surgical prep.

In step 106, surgical prep, the dental health care professional could (after properly anesthetizes the patient and instituting other required dental surgical pre-operation protocols) could make incisions in the gum area of the dental surgical site, and peel back the gum to expose the portion of bone being operated upon. After this step is substantially completed, the process 100 could proceed to step 108, use of the bone foundation guide.

In step 108, use of the bone foundation guide, the bone foundation guide is properly placed upon to the dental surgical site (e.g., its bottom being contoured to match and receive the exposed bone portion) and properly secured to the site (e.g., fasteners passing through the bone foundation guide to anchor into the bone structure of the dental surgical site.) The cutting containment guard could then be attached to the top of the bone foundation guide to create with the bone foundation a cutting slot.

The dental health care professional can then use the bone foundation guide (e.g., BFG) to reduce or augment the bone structure as required utilizing known dental techniques for same to prove the proper bone contour. Once this step is substantially completed, the process 100 could proceed to step 210, use of the dental implant surgical guide.

In step 110, use of the dental implant surgical guide, the dental health care professional could place the bottom side of the dental implant surgical guide upon the top of the bone foundation guide generally enclosing the open surgical space. Fasteners could then penetrate through the surgical guide to embed themselves into the body of the bone foundation guide to secure the surgical guide into place upon the bone foundation guide. In addition or alternatively to this attachment, the fasteners could pass through dental implant surgical guide to directly secure the surgical guide into place upon the dental surgical site. In addition to or alternatively to this attachment, extended fasteners could penetrate through the both bodies of the bone foundation guide and the dental implant surgical guide and into bone of the dental surgical site.

In one embodiment of the invention, prior to the attachment of the dental implant surgical guide to the bone foundation guide, a tissue spacing gasket may be inserted between the prepared dental surgical site and the bottom of the bone foundation guide. This tissue spacing gasket adjusts the combination for the depth of the gum tissue normally present at the dental surgical site but that has been peeled back at the onset of surgical operations.

The dental healthcare professional could use the two guides combined to substantially direct and operated implant preparation accessories or implements (e.g., drills, reamers, and the like) to properly prepare the dental operation site to receive the implant(s) (e.g., pass through the dental implant surgical guide and into the open surgical space. This preparation could ensure the proper orientation and telemetry of the implant accessories into the bone of the dental surgical site. Once the bone is properly prepared, the implant(s) could then pass through the combination to be anchored into the bone. Once this step is substantially completed, the process 100 could proceed to step 112, removal of the guides.

In step 112, removal of the guides, once the implant(s) is (are) properly located in place within the dental surgical site, the fasteners for the bone foundation guide and/or the dental implant surgical guide could be removed to generally allow the combined guides or the guides individually (as well as any tissue space gasket, if used) to be removed from the dental site.

This process 100 could now allow the attachment of trans mucosal abutment, use of temporary cylinder/associated seal/additional filling methods to properly prepare the dental implant for the attachment of prosthesis and the like. At that time, the dental prosthetics could be checked for fitting upon the placed implant(s). If the prosthetics do not need adjustment, they can be removed from the implant and healing abuts can be fitted in their place as required. The gum tissues can then be sutured or otherwise cover-up the exposed bone to meet up with the abutment/implants. If abutments are not required, then the prosthetic could be placed upon the implants in a secure fashion. If the gum tissues need to heal or need to heal around the healing abutments or the implants require ossification to secure them in place to the bone, then after these event(s) have occurred/or a suitable amount of healing time has passed then the prosthetic could be placed upon the implants in a secure fashion. After this step is substantially completed, the process 100 could proceed back to step 102 as needed.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As shown in the specification, drawings, claims and abstract, the invention provides for the combining together as one unit, a bone foundation guide and a dental implant surgical guide that generally are otherwise used separately. By digitally designing the two guides to be combined together, the time, effort, cost and patient recover time can be reduced for dental implant procedure. In further combining the two guides with a tissue spacing gasket, the combination can now take into account the depth of the tissue that otherwise would be present at the dental surgical site. The guides reversibly combination consequentially properly places and secures a dental implant-retained prosthesis in a manner that reduces patient stress and bruising that may occur if the two guides were applied separately. The designing of the guides (and gasket) to be conjoined to generally allow implant appliances, implants and securing/attachment fasteners to pass through the combination onto the bone at a dental surgical guide.

The invention may further provide for cutting containment guard that can attach to the body of the bone foundation guide in place of the dental implant surgical guide. The cutting containment guard in combination with the body of the bone foundation guide

What is claimed is:

1. A bone foundation guide compromising:
A) a bone foundation guide body for guiding a reshaping of an exposed bone at a dental surgical site, the bone foundation guide body having a buccal wall and a lingual wall that is continuously connected by a first end and a second end to form an encircled open surgical space that continuously connects a top and a bottom of the bone foundation guide body, the top being contoured to guide a cutting implement to reshape the exposed bone;

B) a cutting containment guard that attaches to the top of the bone foundation guide body to form a combination of a bone foundation guide body and cutting containment guard, the combination forming a cutting slot that receives and guides a cutting edge of the cutting implement used to reshape the exposed bone at the dental surgical site, the cutting containment guard being removed from the body after the exposed bone is reshaped;

C) a dental implant surgical guide that attaches to the bone foundation guide body in place of the cutting containment guard to direct the placement of one or more implants through the encircled open surgical space;

wherein the bottom of the bone foundation guide body is contoured to reversibly affix to the exposed bone while the top can removably accept the cutting containment guard or in alternative the dental implant surgical guide.

2. The bone foundation guide of claim 1 wherein the cutting slot further comprises one or more non-cutting ends that allow the cutting edge to either engage or disengage from the cutting slot without being in contact with exposed bone.

3. The bone foundation guide of claim 1 wherein the cutting slot further forms a side tool channel that removably accepts and guides a non-cutting portion of the cutting implement.

4. The bone foundation guide of claim 1 further comprising a guide tip that removably attaches to the cutting implement, the guide tip engages a tool side channel as formed by the cutting slot.

5. The bone foundation guide of claim 1 wherein the cutting containment guard further provides a backstop that prevents the cutting edge from making contact with non-dental surgical site portions of the patient's mouth.

6. The bone foundation guide of claim 5 wherein the backstop further comprises a shelf that supports a tip of a blade of a cutting implement that engages the combination.

7. The bone foundation guide of claim 1 wherein the dental implant surgical guide and the bone foundation guide when combined together have aligned passages that allow one or more dental implants to move through the dental implant surgical guide and the bone foundation guide as combined.

8. The bone foundation guide of claim 7 wherein the one or more dental implants moves through the open surgical space.

9. A bone foundation guide comprising:
(A) a bone foundation guide body contoured to guide a cutting implement to alter an exposed bone of a dental surgical site, the bone foundation guide body comprising of a buccal wall and a lingual wall held apart from each another by a first end and second end in a manner that denotes an encircled open surgical space continuously connecting a top and a bottom of the bone foundation guide body, the encircled open surgical space capable of passing one or more dental implants through the bone foundation guide body to the dental surgical site, the bottom is further contoured to affix to the exposed bone of the dental surgical site while the top is further adapted to be attached with a dental implant surgical guide or in the alternative a cutting containment guard; and (B) a cutting containment guard having a cutting channel for receiving the exposed bone when the cutting containment guard is attached to the bone foundation guide body to thereby form a combination, wherein the combination forms a cutting slot for guiding a cutting edge of a cutting implement to alter the exposed bone from the bone foundation guide body.

10. The bone foundation guide of claim 9 wherein the combination further creates a backstop to prevent the cutting edge of the cutting implement from cutting of a non-dental surgical site portion of the patient's mouth.

11. The bone foundation guide of claim 9 wherein the backstop creates a shelf upon which a tip of the cutting edge may ride when the cutting implement engages the combination.

12. The bone foundation guide of claim 9 wherein the formed cutting slot creates a tool open channel for engaging and guiding a non-cutting portion of the cutting implement.

13. The bone foundation guide of claim 9 further comprising a dental implant surgical guide that is configured to replace the cutting containment guard upon the bone foundation guide body after the exposed bone has been altered.

14. The bone foundation guide of claim 13 wherein the dental implant surgical guide as combined with bone foundation guide body is configured to direct implants to pass through the encircled open surgical space.

15. The bone foundation guide of claim 14 further comprising a tissue spacing gasket that is affixed to the bone foundation guide body.

16. The bone foundation guide of claim 15 wherein a combination of the dental implant surgical guide and bone foundation guide body is configured to direct one or more implants to pass through a tissue support gasket.

17. A method of using a bone foundation guide comprising the following steps, but not necessarily in the order shown:
A) providing a bone foundation guide body having a top and a bottom, the bone foundation guide body further forming an encircled open surgical space, wherein the bottom is further contoured to receive and rest upon an exposed bone of a dental surgical site while the top is contoured to guide the alteration of the exposed bone of a dental implant surgical site by a cutting implement, wherein the top is further capable of reversibly attaching a cutting containment guard and in the alternative a dental implant surgical guide;
B) providing a cutting containment guard that, when attached with the bone foundation guide body, forms a cutting slot that is transversely oriented with respect to the open surgical space and that accepts a cutting edge of the cutting implement;
C) removably anchoring the bone foundation guide body upon the exposed bone;
D) attaching the bone foundation guide body and the cutting containment guard together by attaching the cutting containment guard to the bone foundation guide body to form the cutting slot that is transversely oriented with respect to the open surgical space; and
E) altering the exposed bone by inserting the cutting edge of the cutting implement along the path that is transversely oriented with respect to the open surgical space into the cutting slot.

18. The method of claim 17 wherein inserting the cutting edge of the cutting implement along the path that is transversely oriented with respect to the open surgical space into the cutting slot further comprises a step of inserting the cutting edge into the cutting slot of the bone foundation guide body as attached to the dental surgical site without the cutting edge contacting the exposed bone.

19. The method of claim 17 wherein the attached bone foundation guide body and cutting containment guard further form a tool side channel that overlays the cutting slot, the tool side channel capable of removably engaging a non-cutting edge portion of the cutting implement.

20. The method of claim 19 further comprising the step of placing a guide tip as attached to cutting implement into the tool side channel.

* * * * *